United States Patent [19]

Brehob et al.

[11] 4,020,417
[45] Apr. 26, 1977

[54] SOIL MOISTURE INDICATOR DEVICE

[75] Inventors: Alfred W. Brehob, Laguna Beach; Carlos E. Wheeler, Costa Mesa, both of Calif.

[73] Assignee: Turf Service Laboratories, Inc., Stanton, Calif.

[22] Filed: Nov. 26, 1975

[21] Appl. No.: 635,389

[52] U.S. Cl. .............................. 324/65 R; 73/73; 324/65 P; 340/235

[51] Int. Cl.$^2$ ............... G01R 27/02; G01N 27/02

[58] Field of Search ............ 73/73; 324/65 P, 65 R; 340/235; 200/61.04, 61.05

[56] References Cited

UNITED STATES PATENTS

| | | | |
|---|---|---|---|
| 2,437,134 | 3/1948 | Smith | 324/65 P |
| 2,768,028 | 10/1956 | Robinson | 324/65 P |
| 2,793,527 | 5/1957 | Turner | 324/65 P |
| 2,906,952 | 9/1959 | Horecky | 324/65 P |
| 3,882,383 | 5/1975 | Matlin | 324/65 P |
| 3,904,960 | 9/1975 | Niehaus | 324/65 P |
| 3,919,631 | 11/1975 | Brown | 324/65 P |

Primary Examiner—S. Clement Swisher
Assistant Examiner—Denis E. Corr
Attorney, Agent, or Firm—John T. Matlago

[57] ABSTRACT

A soil moisture indicator device for plants comprises an electrical circuit which includes an unbalanced resistive bridge having the common junctions of the resistors on its opposite sides connected to control the switching of a pair of indicator lights. Current drawn through the resistance of the soil as sensed by a probe is used to adjust the output voltages on the sides of the unbalanced resistive bridge to switch on one of the indicator lights if the soil has at least an adequate moisture content and to switch on the other of the indicator lights if the soil has an excessive moisture content.

7 Claims, 7 Drawing Figures

U.S. Patent     April 26, 1977     4,020,417
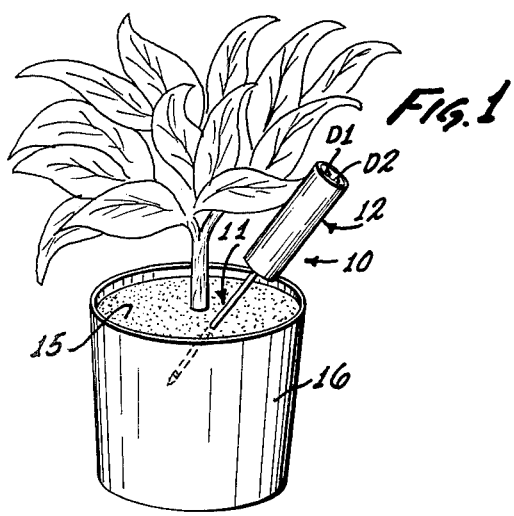
FIG. 1
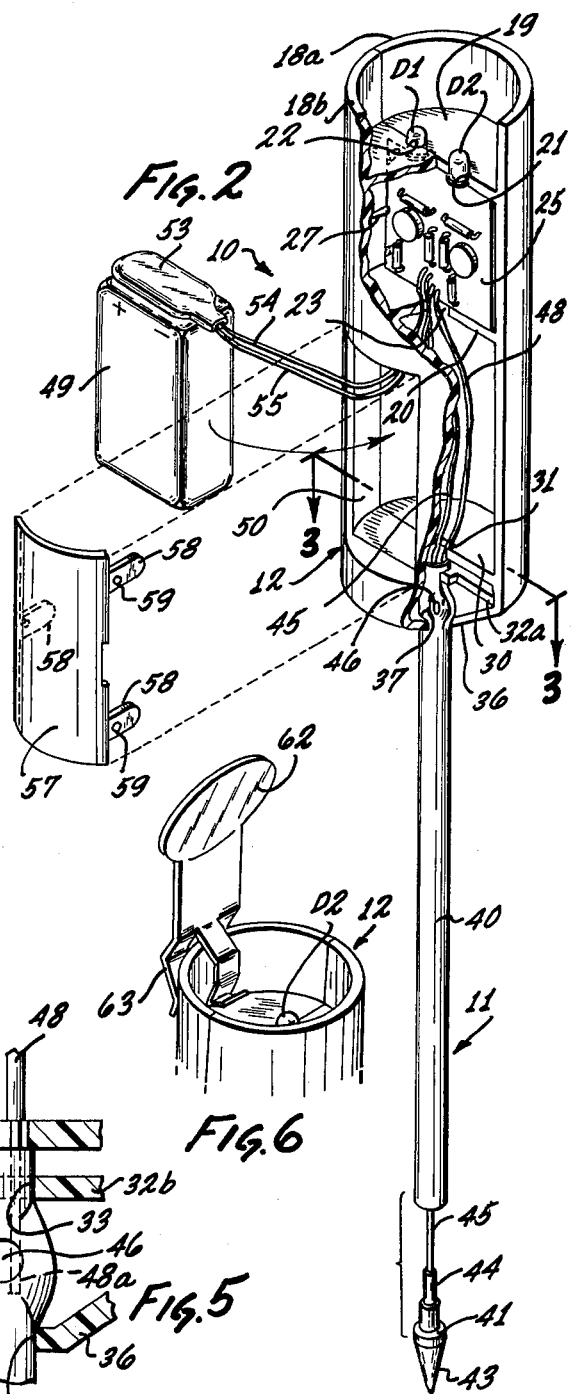
FIG. 2
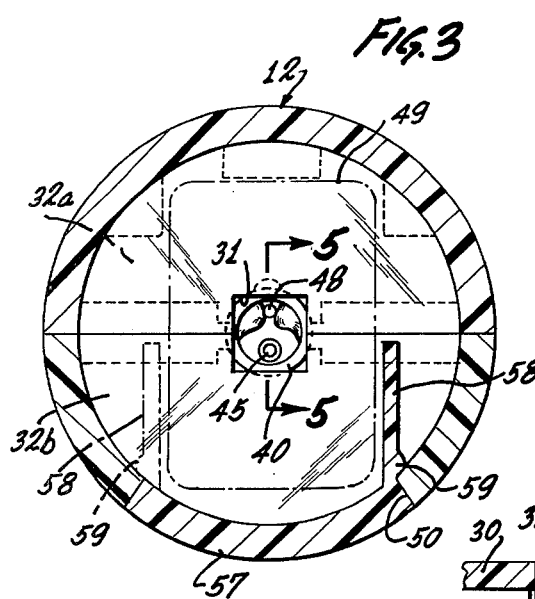
FIG. 3
FIG. 6
FIG. 5
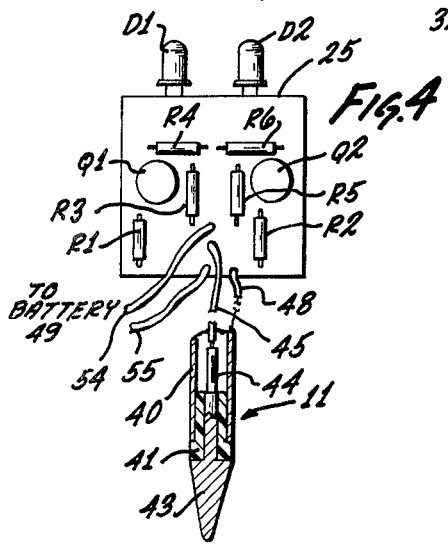
FIG. 4
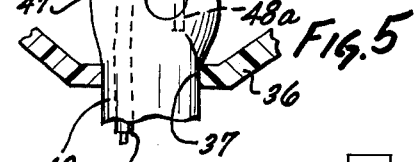
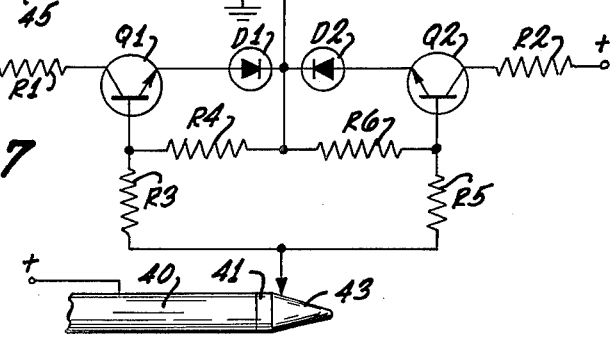
FIG. 7

SOIL MOISTURE INDICATOR DEVICE

This invention relates to a soil moisture indicator device and more particularly to such a device especially adapted for indicating both the adequate and the overwatered condition of the soil in which a plant is growing.

Plants require water and air in the soil to assist them in absorbing minerals which are used to stimulate their growth. The air helps to form with the minerals the desired compounds which are then placed in solution in the water and carried with other material in the soil through the roots and to the leaves of the plant.

Thus if not enough water is added to the soil to replace that which is carried away through the roots of the plant, the plant will not thrive. But just as importantly, if too much water is added to the soil and not able to properly drain away, it fills the minute air spaces between the soil particles. As a consequence, the air is prevented from reaching the minerals in the soil and from combining therewith to form the desired nutrients that the plants need to thrive. If this condition is permitted to continue for any length of time the plant will die. It is thus seen that the maintaining of the proper balance of the air and water in the soil, as well as the keeping of the soil well supplied with the necessary minerals and other nutrients, are important for the plant to be healthy.

The present invention provides a moisture indicator device which indicates if the soil has at least the adequate moisture to keep the plant healthy. The device further indicates if the soil has been overwatered and whether the soil is properly draining to prevent this condition from continuing. The device further can be used to indicate whether the soil needs fertilizing to keep the plant healthy.

Accordingly, one of the objects of the present invention is to provide a simple, highly reliable, easy to use, soil moisture indicator device.

Another object of the present invention is to provide a simple sensing probe for testing soil in the neighborhood of the roots of a plant to indicate a lack of an adequate moisture condition, at least an adequate moisture condition or an excessive moisture condition therein.

Another object of the invention is to provide a solid state circuit which is completed through the soil and responds to the electrical resistance therein to illuminate one or both of a pair of light emitting diodes to indicate the moisture content of the soil.

Still another object of the present invention is to provide an unbalanced resistive bridge circuit which responds to the resistivity of the soil for the purpose of switching on light emitting diodes to indicate the moisture content of the soil.

With these and other objects in view the invention consists of the construction, arrangement and combination of the various parts of the device whereby the objects contemplated are attained as hereinafter more fully set forth, pointed out in the appended claims and illustrated in the accompanying drawings.

DRAWING SUMMARY

FIG. 1 illustrates a potted plant having the soil near its roots tested by the moisture indicator device of the present invention;

FIG. 2 is a partially exploded prespective view of the moisture indicator device with a portion of the housing serving as the handle cut away;

FIG. 3 is a sectional view taken along line 3—3 in FIG. 2;

FIG. 4 is a view of the circuit card with its electrical components and the electrical connections thereto;

FIG. 5 is a fragmentary sectional view taken along lines 5—5 in FIG. 3;

FIG. 6 illustrates a reflector mounted on the upper end of the housing; and

FIG. 7 is a schematic diagram of the electrical circuit.

DESCRIPTION OF PREFERRED EMBODIMENT

Referring to the drawings, the soil moisture indicator device 10 of the present invention includes an elongated metal probe 11 having mounted on the upper end thereof a plastic cylindrical housing 12 which serves as a handle. A pair of light emitting diodes D1 and D2 are located in the recessed upper end of the housing 12. As will be explained hereinafter, when the probe 11 of the device 10 is inserted in the soil 15 of the container 16, either one, both, or neither of the light emitting diodes D1 and D2 become illuminated depending on the moisture content of the soil 15.

As shown in FIG. 2, the housing 12 is formed of two longitudinal half sections 18a and 18b. These half sections when mated together provide an upper transverse wall 19 which is spaced from the upper end of the housing, an intermediate transverse partition 20, and a lower transverse partition 30 which is spaced above the conical bottom 36 of the housing. The upper end wall 19 is provided with a pair of spaced openings 21 and 22 while the intermediate partition 20 and the lower partition 30 are provided with central rectangularly shaped openings 23 and 31, respectively. The bottom 36 of the housing 12 is also provided with a circular opening 37.

Prior to assembly of the half sections 18a and 18b, a printed circuit card 25 having electrical components mounted on the surface thereof is seated in the vertically disposed opening of the half section 18a formed by its upper end wall 19, its intermediate partition 0, and its outer side walls. The light emitting diodes D1 and D2 are connected on the upper end of the circuit card 25 so as to fit in the openings 21 and 22 provided on the upper end wall 19. The inner side wall surfaces of the housing half sections are provided with projections 27 to help to securely position the circuit card 25 within the housing.

Spaced a short distance below the lower partition 30, one on each of the half sections of the housing 12, are a pair of transversely spaced support members 32a and 32b whose opposing central portions are shaped to define a circular opening 33 similar to that provided on the bottom 36. Support members 32a and 32b are spaced above the bottom 36 of the housing and provide a support for the upper end of the probe 11.

The probe 11 includes an elongated conductive tubular member 40, an insulating spacer 41, and a conductive tapered end member 43. The members 40 and 43 are preferably made of aluminum. The insulated spacer 41 is provided with a reduced diameter 42 on its upper end which is securely fitted within the lower end of the tubular member 40. The tapered end member 43 is formed with a pin 44 on its upper end which extends with a tight fit through the insulating spacer 41 so as to connect to and make electrical contact with the free end of a first insulated conductor 45 extending down from the circuit card 25. The free end 48a of a second insulated conductor 48 extending down from the circuit card is inserted into the upper end of the tubular member 40 and secured to make electrical contact therewith by permanently flattening the tubular member at point 46. As shown in FIG. 5 this deforms the adjacent portion 47 of the wall of the tubular member causing it to bulge outwardly.

During assembly the upper end of the tubular member 40 is fitted into the circular openings in the bottom portion of the half section 18a of the housing such that the upper edge of the tubular member 40 bears against the bottom of the lower partition 30. When so positioned the bulging wall portion 47 of the tubular member snugly fits in the space between the support members 32a and 32b and the bottom 36 of the half section 18a. The half sections 18a and 18b are then mated together and sealed by the use of heat and pressure. It should be noted that the tubular member 40 is securely held so that it can not bend or more axially relative to the housing 12. Furthermore, the circuit card 25 is securely held in position with the light emitting diodes D1 and D2 extending through the openings 21 and 22 in the upper end wall 19 and into the recess formed on the upper end of the housing. Such a construction helps to protect the light emitting diodes. When the device 10 is being used to test the soil in hanging plants, it may be difficult to see the light emitting diodes in the recess. Accordingly, a reflector 62 may be provided having a clip arrangement 63 for mounting on the upper rim of the housing.

An access opening 50 is provided on the sidewall of the housing half section 18b to the compartment formed therein between the intermediate partition 20 and the lower partition 30. The opening 50 enables a battery 49 to be placed in the housing after its positive and negative terminals have been connected to a battery cap 53 which is flexibly connected by conductors 54 and 55 to the circuit board 25. An access panel 57 has fingers 58 on the sides thereof with buttons 59 which enable the panel to be snapped into position to cover the access opening 50.

The printed circuit card 25 has electrical components mounted thereon by solder, for example, to thus provide the electrical circuit used to indicate the moisture content of the soil in which a plant is growing. The electrical circuit, as schematically shown in FIG. 7, includes two indicator circuits connected across the positive and negative terminals of a 9 volt battery 49. Note that ground in the circuit corresponds to the negative terminal of the battery 49. A first indicating circuit comprises a limiting resistor R1 connected to the collector of a transistor Q1 and a light emitting diode D1 whose anode is connected to the emitter of transistor Q1 and whose cathode is grounded. A second indicator circuit comprises a limiting resistor R2 connected to the collector of a transistor Q2 and a light emitting diode D2 whose anode is connected to the emitter of transistor Q2 and whose cathode is grounded.

Each of the transistors Q1 and Q2 functions in its respective indicating circuit as a switch in that, when open, i.e., non conducting, it prevents current from conducting through its associated light emitting diode and when closded, i.e., conducting, permits current to conduct through its associated light emitting diode.

The remaining resistors on the circuit card 25 define an unbalanced resistive bridge circuit whose circuit path to the positive terminal of the battery is completed through the electrolytic action of the minerals in solution in the soil adjacent the insulating spacer 41 on the probe 11. The common junction of the pair of resistors comprising each of the opposite sides of the bridge circuit provide the outputs of the bridge circuit which are connected to bias the bases of the respective transistors Q1 and Q2 to cause them to become conductive when the resistance of the path through the soil as sensed by the probe 11 reaches values indicative of an adequate moisture condition and an excessive moisture condition, respectively.

Describing the electrical circuit more particularly, the positive terminal of the battery 49 is connected to the tubular member 40 at its flattened point 46. The tapered end member 43 of the probe 11 is connected by its pin 44 to one end of each of the parallel resistors R3 and R5, the other ends of which are respectively connected to the bases of the transistors Q1 and Q2. A resistor R4 is then connected between the base of transistor Q1 and ground and a resistor R6 is connected between the base of transistor Q2 and ground.

As previously mentioned, the circuit from the positive terminal of the battery to the bridge is completed through the soil. Thus as the moisture of the soil varies, its resistance varies due to the electrolytic properties of the soil and causes the voltages on the bases of the transistors Q1 and Q2 to vary. The resistors R3 and R4 are selected such that it is not until the moisture content is at least adequate that the voltage on the common junction of these resistors as applied on the base of transistor Q1 is sufficiently high to overcome the forward bias of the transistor Q1 and the light emitting diode D1 such as to illuminate this light emitting diode. The light emitting diode D1 only will thus become illuminated as long as the soil is not saturated with water. In other words, for the resistance in the soil just below the point of saturation, the voltage on the common junction of resistors R5 and R6, as applied on the base of transistor Q2, is still too low to overcome the forward bias of the transistor Q2 and the light emitting diode D2. Now then if the plant is given a saturation watering which is indicative of an excess moisture condition of the soil, the voltage on the common junction of resistor R5 and R6 as applied on the base of the transistor amplifier Q2 rises so as to overcome the forward bias of the transistor Q2 and the light emitting diode D2 such as to illuminate the light emitting diode D2. Now then both light emitting diodes D1 and D2 are turned on, i.e., illuminated. It should be understood that once light emitting idode D1 turns on it remains on alone as the moisture content of the soil is within the range of the adequate determination which extends from a minimum point to a point just short of saturation watering of the plant. Likewise, the light emitting diode D2 does not turn on until the moisture content reaches the excess condition, i.e., the saturation condition.

The values of the resistors in the respective indicating circuits and the respective bias circuits of the transistors Q1 and Q2 are chosen to cause the soil moisture indicator device 10 to operate in the above described desired manner. Thus, in the illustrated embodiment, the below listed resistor values are provided. It is inderstood that these values are given by way of example and are not limiting.

| Resistor | Resistor Value |
| --- | --- |
| R1 | 1,000 ohms |
| R2 | 560 ohms |
| R3 | 1,000 ohms |
| R4 | 4,700 ohms |
| R5 | 6,800 ohms |
| R6 | 10,000 ohms |

Recommended operation of the moisture indicator device 10 for testing a plant is as follows. The probe 11 is inserted about half way to the bottom of the plant container 16. If neither of the two light emitting diodes D1 or D2 is illuminated the soil is too dry and the plant should be given a good saturation watering. It has been determined that a plant thrives best if it goes through a cycle from a saturation watering condition to a dry condition. Thus if only the light emitting diode D1 is illuminated the moisture content of the soil is just right and no more water should be added. If both light emitting diodes D1 and D2 become illuminated the moisture content of the soil is excessive. This, of course, will occur right after a saturation watering and should be of no concern at that time since that is normal. However, if this indication on the device 10 continues on to the next day, for example, it is indicative that the water may not be draining properly and if permitted to continue can cause the plant to die.

It should be noted that it may happen that even after a saturation watering of the plant only one indicator light D1 is illuminated. This is an indication that soil nutrients are inadequate and plant food should be added. It should now be clear that the second light emitting diode not only indicates the saturation watering condition of the soil when it becomes illuminated, but when the light emitting diode D2 does not illuminate after a saturation watering, it provides an indication that the nutrient level of the soil is low and fertilizer or plant food should be added.

It should be further noted that if the moisture indicator device 10 has been in use for some time the battery 49 may be weak. This condition may cause only light emitting diode D1 to be illuminated after the plant has received a saturation watering and even if the nutrient level is adequate. To test the battery, the probe is inserted into a container of ordinary tap water (processed or distilled water should not be used). If the battery is in good condition both light emitting diodes become illuminated. If only one light emitting diode becomes illuminated, the battery is weak and must be replaced.

Although a preferred embodiment of the invention has been illustrated and described in detail, it will be apparent to those skilled in the art that various modifications may be made therein without departing from the spirit of the invention or from the scope of the appended claims.

What is claimed is:

1. An indicating device for testing the moisture content of soil about the roots of a plant comprising:
   a power supply,
   a first indicator circuit connected across said power supply and including a first semiconductor switching means in series with a first indicator light,
   a second indicator circuit connected across said power supply and including a second semiconductor switching means in series with a second indicator light,
   control circuit means connected across said power supply with its current path completed through the soil to be tested, said control circuit means comprising an unbalanced resistive bridge having junctions on the opposite sides thereof respectively providing output voltages for controlling said first and second semiconductor switching means,
   whereby said control circuit means adjusts the output voltages on said junctions in response to the resistivity of the soil to cause one of the semiconductor switching means to conduct to illuminate its associated indicator light if the moisture content of the soil is at least adequate and to cause the other said semiconductor switching means to conduct to illuminate its associated indicator light if the moisture content of the soil is excessive.

2. The invention is accordance with claim 1 wherein said first and second indicator lights are light emitting diodes.

3. An indicating device for testing the moisture content of soil about the roots of a plant comprising:
   a power supply,
   a first indicator circuit connected across said power supply and including a first transistor having a first indicator light connected in the collector-emitter path thereof,
   a second indicator circuit connected across said power supply and including a second transistor having a second indicator light connected in the collector-emitter path thereof, and
   control circuit means connected across said power supply with its current path completed through the soil to be tested, said control circuit means comprising an unbalanced resistive bridge having the common junctions of the pairs of resistors on opposite sides thereof connected to the bases of the respective transistors,
   said control circuit means being operative to provide a first bias voltage on the base of said first transistor to cause it to conduct to illuminate said first indicator light when the resistance of said soil is indicative of at least an adequate moisture content therein and being operative to provide a second bias voltage on the base of said second transistor to cause it to conduct to illuminate said second indicator light when the resistance of said soil is indicative of an excessive moisture content therein.

4. A device for indicating the moisture content of the soil about the roots of a plant comprising:
   a probe including a conductive tubular member and a conductive end member interconnected by an insulating spacer,
   a hollow handle mounted on the upper end of said probe,
   said hollow handle including therein a battery and a printed circuit card, and
   said hollow handle having a pair of light emitting diodes positioned in a pair of openings in the wall thereof,
   said circuit card having circuit means thereon connected to said battery, said pair of light emitting diodes, said tubular member and said end member,
   said circuit means comprising a first indicator circuit including a first transistor having one of said light emitting diodes connected in the collector-emitter path thereof, a second indicator circuit including a second transistor having the other of said light emitting diodes connected in the collector-emitter path thereof, and an unbalanced resistive bridge connecting to said end member and having its circuit through the tubular member to the power supply completed through the soil in which the probe is inserted, the common junctions of adjacent resistors on the opposite sides of said bridge connected to provide voltages for biasing the bases of the respective transistors, whereby when said probe is inserted into the soil said circuit means responds to the resistivity of the soil to cause one of said light emitting diodes to become illuminated if the moisture content of the soil is at least adequate and to cause the other of said light emitting diodes to become illuminated if the moisture content of the soil is excessive.

5. The invention is accordance with claim 4 wherein said handle includes a battery access opening having a readily removable cover panel therefor.

6. The invention in accordance with claim 4 wherein said printed circuit card is mounted to lie in an axial plane within said hollow handle.

7. The invention in accordance with claim 4 wherein said light emitting diodes are positioned in a pair of openings provided in a recessed portion of the wall of the handle.

* * * * *